US009332930B2

(12) United States Patent
Chantz

(10) Patent No.: US 9,332,930 B2
(45) Date of Patent: *May 10, 2016

(54) USE OF A SUPPORT DEVICE

(71) Applicant: International Business Machines Corporation, Armonk, NY (US)

(72) Inventor: Hyman D. Chantz, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 226 days.

This patent is subject to a terminal disclaimer.

(21) Appl. No.: 14/156,672

(22) Filed: Jan. 16, 2014

(65) Prior Publication Data
US 2014/0135656 A1    May 15, 2014

Related U.S. Application Data

(63) Continuation of application No. 13/739,077, filed on Jan. 11, 2013, now Pat. No. 8,641,645, which is a continuation of application No. 12/014,842, filed on Jan. 16, 2008, now Pat. No. 8,372,018.

(51) Int. Cl.
*A61B 5/00*    (2006.01)
*A61B 5/11*    (2006.01)

(52) U.S. Cl.
CPC ............. *A61B 5/1116* (2013.01); *A61B 5/0053* (2013.01); *A61B 5/1126* (2013.01); *A61B 5/442* (2013.01); *A61B 5/6801* (2013.01); *A61B 5/6814* (2013.01); *A61B 5/6828* (2013.01); *A61B 5/6887* (2013.01); *A61B 5/704* (2013.01); *A61B 5/72* (2013.01)

(58) Field of Classification Search
CPC ........ A61B 5/11; A61B 5/112; A61B 5/1116; A61B 5/103; A61B 5/1032; A61B 5/0053
See application file for complete search history.

(56) References Cited

U.S. PATENT DOCUMENTS

| 5,833,633 | A | 11/1998 | Sarvazyan |
|---|---|---|---|
| 5,853,005 | A | 12/1998 | Scanlon |
| 6,485,441 | B2 | 11/2002 | Woodward |
| 6,511,427 | B1 | 1/2003 | Sliwa et al. |
| 6,899,103 | B1 | 5/2005 | Hood et al. |

(Continued)

OTHER PUBLICATIONS

Bartkowski et al.; Surgical Care in the 2ast Century; JAOA; Dec. 2005; pp. 545-549; vol. 105, No. 12.

(Continued)

*Primary Examiner* — Max Hindenburg
(74) *Attorney, Agent, or Firm* — Schmeiser, Olsen & Watts, LLP; Matthew Chung

(57) ABSTRACT

A method and system for determining a pose of a subject. The subject is placed onto a surface of a platform having a first radio-frequency transceiver and a second radio-frequency transceiver. A first radio-frequency transponder is placed onto an upper extremity of the subject. A second radio-frequency transponder is placed onto a lower extremity of the subject. A first signal is transmitted from the first transceiver to the first transponder, resulting in the first transponder sending a second signal. A third signal is transmitted from the second transceiver to the second transponder, resulting in the second transponder sending a fourth signal. The second signal is received by the first transceiver. The fourth signal is received by the second transceiver. A pose of the subject is determined based on receiving the second signal and the fourth signal.

20 Claims, 5 Drawing Sheets

(56) References Cited

U.S. PATENT DOCUMENTS

| | | | |
|---|---|---|---|
| 6,984,207 | B1 | 1/2006 | Sullivan et al. |
| 7,183,930 | B2 | 2/2007 | Basir et al. |
| 7,347,538 | B2 | 3/2008 | Mita |
| 7,374,538 | B2 | 5/2008 | Nightingale et al. |
| 2004/0260156 | A1 | 12/2004 | David et al. |
| 2006/0063982 | A1 | 3/2006 | Sullivan et al. |
| 2006/0226957 | A1 | 10/2006 | Miller et al. |
| 2006/0246921 | A1 | 11/2006 | Russ |
| 2007/0132597 | A1 | 6/2007 | Rodgers |
| 2007/0136102 | A1 | 6/2007 | Rodgers |
| 2009/0182247 | A1 | 7/2009 | Chantz |
| 2013/0131556 | A1 | 5/2013 | Chantz |

OTHER PUBLICATIONS

Smart Technology: Aiding Diagnosis and Productivity [online]; 1 page; [retrieved on Jul. 24, 2007]; retrieved from the Internet: <URL: http://www.medicalimagingorg/future/technology.cfm>.

Gardner, E., writer; Purdue Researchers Develop Technology to Detect Cancer by Scanning Surface Veins; [online]; 3 pages; [retrieved on Sep. 7, 2007]; retrieved from the Internet: <URL: http://news.uns.purdue.edu/x/2007b/070904LowPNAS.html>.

Ho; A Prototype on RFID Sensor Networks for Elder Healthcare: Progress Report; IGCOMM; Aug. 26, 2005; pp. 70-72.

Office Action (Mail Date Jul. 21, 2008) for U.S. Appl. No. 12/014,842, filed Jan. 16, 2008.

Office Action (Replacement) (Mail Date Aug. 6, 2008) for U.S. Appl. No. 12/014,842, filed Jan. 16, 2008.

Amendment filed Nov. 6, 2008 in response to Office Action (Mail Date Aug. 6, 2008) for U.S. Appl. No. 12/014,842, filed Jan. 16, 2008.

Office Action (Mail Date Jan. 15, 2009) for U.S. Appl. No. 12/014,842, filed Jan. 16, 2008.

Amendment filed Apr. 14, 2009 in response to Office Action (Mail Date Jan. 15, 2009) for U.S. Appl. No. 12/014,842, filed Jan. 16, 2008.

Final Office Action (Mail Date Aug. 11, 2009) for U.S. Appl. No. 12/014,842, filed Jan. 16, 2008.

Notice of Appeal filed Nov. 10, 2009 in response to Final Office Action (Mail Date Jan. 15, 2009) for U.S. Appl. No. 12/014,842, filed Jan. 16, 2008.

Appeal Brief filed Jan. 7, 2010 for U.S. Appl. No. 12/014,842, filed Jan. 16, 2008.

Office Action (Mail Date Mar. 26, 2010) for U.S. Appl. No. 12/014,842, filed Jan. 16, 2008.

Notice of Appeal filed Jun. 23, 2010 in response to Office Action (Mail Date Mar. 26, 2010) for U.S. Appl. No. 12/014,842, filed Jan. 16, 2008.

Appeal Brief filed Jun. 25, 2010 for U.S. Appl. No. 12/014,842, filed Jan. 16, 2008.

Examiner's Answer (Mail Date Sep. 15, 2010) in response to Appeal Brief filed Jun. 25, 2010 for U.S. Appl. No. 12/014,842, filed Jan. 16, 2008.

Reply Brief filed Nov. 15, 2010 in response to Examiner's Answer (Mail Date Sep. 15, 2010) for U.S. Appl. No. 12/014,842, filed Jan. 16, 2008.

Notice of Allowance (Mail Date Oct. 9, 2012) for U.S. Appl. No. 12/014,842, filed Jan. 16, 2008.

Supplemental Notice of Allowability (Mail Date Nov. 27, 2012) for U.S. Appl. No. 12/014,842, filed Jan. 16, 2008.

Notice of Allowance (Mail Date Sep. 23, 2013) for U.S. Appl. No. 13/739,077, filed Jan. 11, 2013.

Response (Jul. 17, 2013) for U.S. Appl. No. 13/739,077, filed Jan. 11, 2013.

Office Action (Mail Date Apr. 19, 2013) for U.S. Appl. No. 13/739,077, filed Jan. 11, 2013.

USE OF A SUPPORT DEVICE

This application is a continuation application claiming priority to Ser. No. 13/739,077, filed Jan. 11, 2013, now U.S. Pat. No. 8,641,645, issued Feb. 4, 2014, which is a continuation of Ser. No. 12/014,842, filed Jan. 16, 2008, U.S. Pat. No. 8,372,018, issued Feb. 12, 2013.

FIELD OF THE INVENTION

The invention generally relates to methods and devices for supporting and palpating a subject.

BACKGROUND OF THE INVENTION

Rapid, accurate, and cost-effective medical diagnosis, evaluation, and monitoring are important in patient care. Relatively recent requirements include the capability for local, remote, and in-transit patient assessments. Patients and victims of chemical or biological weapons may pose a health risk to medical personnel responsible for examination and diagnosis. Recent threats of world-wide viral epidemics, and chemical and biological acts of terrorism may require rapid correlation and identification of disease outbreaks and vectors, and a means of reducing particular dangers in the use of highly-trained medical personnel for exposure to wide numbers of patients during disease and injury screening, such as in a mass casualty situation.

SUMMARY OF THE INVENTION

The present invention relates to a subject pose determining method comprising:
  placing a subject onto a surface of a platform, said platform having a first radio-frequency transceiver located at a first location on said surface and a second radio-frequency transceiver located at a second location on said surface, wherein said subject is a human being;
  placing a first radio-frequency transponder onto an upper extremity of said subject;
  placing a second radio-frequency transponder onto a lower extremity of said subject;
  transmitting a first radio-frequency signal from said first radio-frequency transceiver to said first radio-frequency transponder on said upper extremity of said subject, resulting in said first radio-frequency transponder sending a second radio-frequency signal to said first radio-frequency transceiver;
  transmitting a third radio-frequency signal from said second radio-frequency transceiver to said second radio-frequency transponder on said lower extremity of said subject, resulting in said second radio-frequency transponder sending a fourth radio-frequency signal to said second radio-frequency transceiver;
  receiving by said first radio-frequency transceiver said second radio-frequency signal;
  receiving by said second radio-frequency transceiver said fourth radio-frequency signal; and
  determining a pose of said subject based on said receiving said second radio-frequency signal and said receiving said fourth radio-frequency signal.

The present invention relates to a palpation method, comprising:
  placing a subject horizontally onto a transducer array disposed on a surface of a support device, said transducer array disposed between said support device and said subject, said transducer array comprising a plurality of piezoelectric transducers, wherein said subject is a human being;
  sending a first signal to at least one piezoelectric transducer of said plurality of piezoelectric transducers, each piezoelectric transducer of said at least one piezoelectric transducer in direct contact with a portion of external tissue of said subject, resulting in said each piezoelectric transducer actuating and exerting a first force against said portion of external tissue; and
  receiving from said each piezoelectric transducer a second signal in response to said exerting said first force against said portion of external tissue, said second signal resulting from a second force exerted by said portion of external tissue against said each piezoelectric transducer in response to said each piezoelectric transducer exerting said first force.

The present invention relates to a palpation device, comprising:
  a platform configured to support a subject;
  a transducer array disposed on a surface of said platform, said transducer array disposed between said platform and said subject, said transducer array comprising a plurality of piezoelectric transducers;
  a first radio-frequency transceiver located at a first location on said surface, said first radio-frequency transceiver configured to receive radio-frequency signals from a first radio-frequency transponder;
  a second radio-frequency transceiver located at a second location on said surface radio-frequency transceiver configured to receive radio-frequency signals from a second radio-frequency transponder; and
  a control system operably coupled to said first radio-frequency transceiver and said second radio-frequency transceiver, said control system coupled to said transducer array and configured to direct each piezoelectric transducer of said plurality of piezoelectric transducers to actuate, said control system configured to receive data from said first radio-frequency transducer and said second radio-frequency transducer, said data relating to said radio-frequency signals from said first radio-frequency transponder, said data relating to said radio-frequency signals from said second radio-frequency transponder.

BRIEF DESCRIPTION OF THE DRAWINGS

The features of the invention are set forth in the appended claims. The invention itself, however, will be best understood by reference to the following detailed description of illustrative embodiments when read in conjunction with the accompanying drawings.

DETAILED DESCRIPTION OF THE INVENTION

Figure 1:
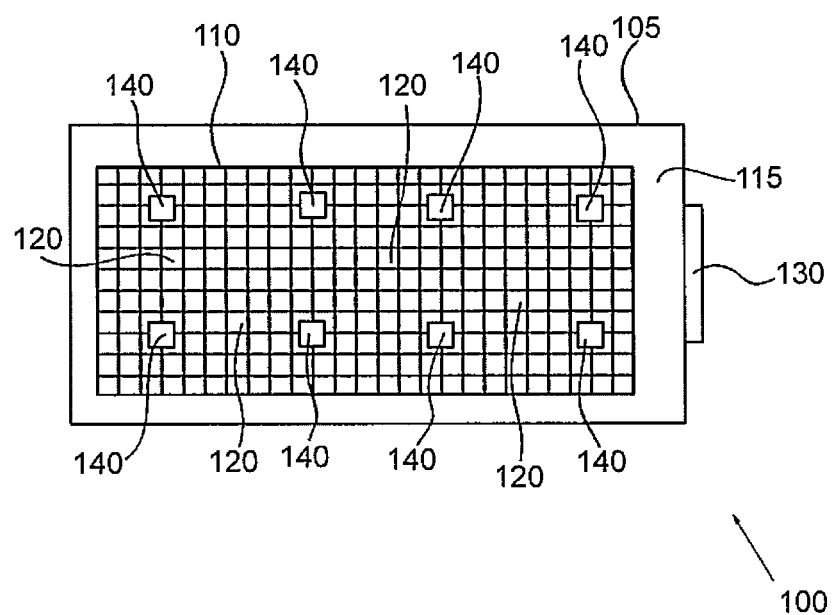
FIG. 1 is an illustration of a support device, in accordance with embodiments of the present invention.

Although certain embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as examples of embodiments. The features and advantages of the present invention are illustrated in detail in the accompanying drawings, wherein like reference numerals refer to like elements throughout the drawings. Although the drawings are intended to illustrate the present invention, the drawings are not necessarily drawn to scale.

FIG. 1 is an illustration of an example of a support device 100, comprising a platform 105. The support device 100 may be configured to support a subject (such as a patient) disposed on a surface 115 of the platform 105. The subject may be supported on the surface 115 while the subject is lying essentially horizontally on the surface 115, for example. For example, the support device 100 may be part of or comprise a gurney or hospital patient stretcher on which patients receiving medical care may be supported, treated, transported, or a combination of these. The support device 100 may be configured to be attached to a medical gurney or stretcher, such as with interlocking structures, clamps, straps, etc. The subjects described herein may be human beings. It is recognized that the devices and methods described herein may be utilized in conjunction with non-human subjects such as in the example of veterinary care of animals, such as non-human primates, for example.

The support device 100 may comprise a sensor array 110 disposed on the surface 115. The sensor array 110 may comprise a plurality of sensor units 120. The sensor array 110 may comprise a transducer array, wherein each sensor unit 120 of the plurality of sensor units comprises a transducer. Each sensor unit 120 of the plurality of sensor units 120 may comprise a piezoelectric transducer. The piezoelectric transducers described herein may be configured such that the piezoelectric transducers transmit an electrical voltage signal when pressure is applied to the transducer, wherein the piezoelectric transducer may behave as a piezoelectric sensor capable of measuring the applied pressure. The piezoelectric transducer described herein may be configured such that a portion of the transducer is moved upon receiving an electrical voltage signal, wherein the piezoelectric transducer may behave as a piezoelectric actuator or piston which may apply a directional force through movement of the portion of the piezoelectric transducer. The range of movement of the piezoelectric transducer may be in a range from about 0 centimeters (cm) to about 2 cm, for example, about 1 cm.

The sensor array 110 may comprise a plurality of sensor units 120, wherein the number of sensor units 120 may be in a range between about 2 and about 500 sensor units, such as about 450 sensor units. The sensor units 120 may be hingedly interconnected or attached in a manner such that the sensor array 110 comprises a single sheet or grid, where the sheet is flexible due to the hinged connection between adjacent sensor units 120. The sheet may be sufficiently flexible so as to essentially conform to an exterior surface of a subject laying on the sensor array 121. The sensor units 120 may comprise square or octagonal surfaces which may be allow for arranging the sensor units 120 into a sensor sheet in a tessellated or grid pattern.

The support device 100 may comprise at least one control system 130, operably coupled to the sensor array 110, sensor units 120 of the sensor array 110, and components of the support device 100 (vide infra), where the control system may be physically coupled to the support device 100 or may be wirelessly coupled such as through a wireless telecommunication connection. The control system 130 may be configured such that the control system may receive, detect, and process signals (such as electrical, light, sound, etc.) received from the sensor array 110, sensor units 120, and components of the support device 100. The control system 130 may convert the received signals into data representative of the signals, and to analyze the representative data, where the data may be stored in a memory storage device or transmitted by the control system to an external computer system or display screen. The control system 130 may direct the activation and operation of components of the support device 100, such as receiving signals from and transmitting signals to the sensor units 120 and other components, where a user may interact with the control system 130, through wired or wireless communication devices, to direct or control components of the support device 130. For example, where the plurality of sensor units 120 comprises a plurality of piezoelectric transducers, the control system 130 may direct at least one piezoelectric transducer of the plurality of piezoelectric transducers to actuate by sending a signal to each piezoelectric transducer of the at least one piezoelectric transducer. The control system 130 may automatically control the components of the support device 100 through an algorithm stored in memory of the control system 130 and based on data received from RF transceivers 140, RF transponders, the sensor array 110, commands from a user through wired or wireless communication, and combinations of these. Data relating to the location of each sensor unit 120 of the sensor array 110 may be stored in the control system 130 such that the control system 130 may direct the actuation of individual or groups of sensor units 120 based on commands received directing sensor unit actuation in a desired location on the support device 130.

The control system 130 may comprise a communication device for transmitting data, sending commands, receiving commands from a remote location, or a combination of these. The communication device may be a wired device such as a telephone line, cable line, etc. or wireless telecommunications device such as a wireless telephone, satellite telephone, shortwave radio, etc.

The support device 100 may further comprise at least one radio-frequency (RF) transceiver 140 configured such that the at least one RF transceiver may receive and transmit RF signals. Each of the at least one RF transceivers 140 may be operably coupled to an antenna. The radio-frequency transceivers described herein may transmit and receive RF signals through the antenna. In some embodiments, the at least one RF transceiver 140 comprises at least two RF transceivers 140. In some embodiments, the at least one RF transceiver 140 comprises a plurality of RF transceivers such as 2, 4, 6, 8, 10, and 12 RF transceivers. The at least one RF transceiver 140 may be disposed on the platform 105. The at least one RF transceiver 140 may be configured such that the at least one RF transceiver may transmit a first radio-frequency signal to at least two radio-frequency transponders, where the at least two radio-frequency transponders are configured such that the at least two radio-frequency transponders may receive the first radio-frequency signal and transmit a second radio frequency signal in response to receiving the first radio-frequency signal, and wherein the at least one RF transceiver 140 is configured such that the at least one RF transceiver 140 receives the second radio-frequency signal. Each radio-frequency transponder may, for example, be a radio-frequency identification (RFID) tag known in the art and capable of receiving at least one RF signal from a RF transceiver and then transmitting a second RF signal in response to receiving the first RF signal. The RFID tag may comprise a microchip encoded with an algorithm capable of deciphering received RF signals and directing the RFID tag to transmit an appropriate RF signal in response, such as an RF signal comprising data identifying the RFID tag.

The at least one RF transceiver 140 may be operably connected to the control system 130, where the at least one RF transceiver 140 may transmit signals to the control system 130 and receive signals from the control system 130, where the control system 130 may transform the received signals into data and analyze and/or store the data, where the data may represent information relating to locations of the at least two radio frequency transponders in relation to the at least one RF transceiver 140 (such as distance and direction from the at least one RF transceiver 140), information identifying each of the at least two radio frequency transponders, or a combination of these.

The control system 130 may comprise a computer system configured such that the control system 130 may analyze data relating to signals received by the control system 130, such as signals received from the sensor array, RF transceivers 140, external computer systems, users, combinations of these, etc. The computer system may analyze the data based on receiving commands from a user. The computer system may have a computer program stored therein, where the compute program may be configured such that the computer system may analyze the data from the RF transceivers 140 based on receiving remote commands from a user, such as commands sent through a wired or wireless telecommunication system. The control system 130 may be configured such that the control system 130 may direct at least one sensor unit 120 of the plurality of sensor units 120 of the sensor array 110 to actuate based on the data received from RF transceivers 140, where the received data may represent the pose of a subject laying on the support device 100. The term "pose", as used herein, is defined as the posture of a subject's body and extremities with respect to the support device on which the subject's body is disposed. For example, a subject may have a pose where the subject is laying essentially horizontally on their back on a support device and where the subject's head is located at one end of the support device and the subject's feet are located a second end. In another example, a subject may have a pose where the subject is laying on their side on a support device with the subject's knees pulled up to the subject's chest, where the subject's head is located at one end of the support device and the subject's feet are location in the middle of the support device. Is it understood that in addition to the examples above of poses a subject may have while disposed on the support devices disclosed herein, there exists a large number of possible poses of a subject, all of which are intended to be included within the scope of the disclosure.

For example, a physician at a remote location, examining a patient lying on a support device as described herein where each sensor unit comprises a piezoelectric transducer, may send commands to the controller to palpate an upper extremity of the patient by determining the location of the patients upper extremity. The control system (or computer system therein) may analyze data received from the RF transceivers and determine the location of the patient's upper extremity (vide infra). Base on the analyzed data, the controller may then direct the actuation of sensor units in contact with the upper extremity of the subject, where the number of sensor units to be actuated may be dictated by a preset value, a command from the user, or a combination of these.

Figure 2:
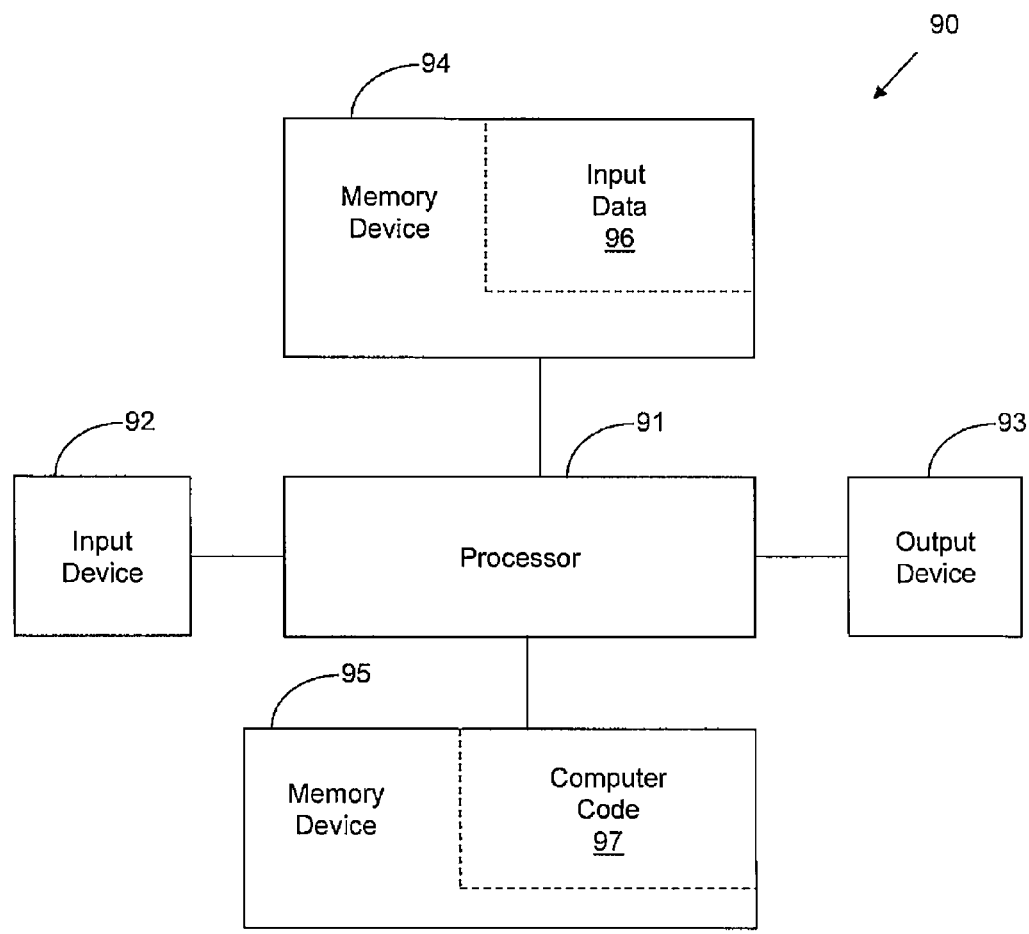
FIG. 2 is an illustration of an example of a computer system, in accordance with embodiments of the present invention.

FIG. 2 is an illustration of an example of a computer system 90 as described herein. The computer system 90 comprises a processor 91, an input device 92 coupled to the processor 91, an output device 93 coupled to the processor 91, and computer-readable storage media 94 and 95 each coupled to the processor 91. The input device 92 may be, inter alia, a keyboard, a mouse, a microphone, a touch sensitive computer screen, a joystick, a combination of these, etc. The output device 93 may comprise, inter alia, a printer, a plotter, a computer display screen or monitor, a magnetic tape, a removable hard disk, a floppy disk, a combination of these, etc. The output device may comprise a communication device, such as a phone modem, a wireless modem, a cable modem, a digital subscriber line (DSL) modem, an Ethernet connection with an network interface card (NIC), etc., or a combination of these which may connect to the communications network 130. The computer-readable storage media 94 and 95 may comprise, inter alia, memory devices such as a hard disk, a floppy disk, a magnetic tape, an optical storage such as a compact disc (CD) or a digital video disc (DVD), a dynamic random access memory (DRAM), a read-only memory (ROM), a flash memory data storage device such as a universal serial bus (USB) flash drive, etc. The computer-readable storage medium 95 may include a computer code 97 which is a computer program that comprises computer-executable instructions. The computer code 97 may include algorithms for analyzing data received from RF transceivers, for determining a pose of a subject based on the analyzed data, for directing the piezoelectric transducers to actuate, or a combination of these. The processor 91 may execute the computer code 97. The computer-readable storage medium 94 may include input data 96. The input data 96 may include input required by the computer code 97. The output device 93 may display output from the computer code 97. Either or both computer-readable storage media 94 and 95 (or one or more additional computer-readable storage media not shown in FIG. 2) may be used as a computer usable medium (or a computer readable medium or a program storage device) having a computer readable program embodied therein and/or having other data stored therein, wherein the computer readable program comprises the computer code 97. Generally, a computer program product (or, alternatively, an article of manufacture) of the computer system 90 may comprise said computer usable medium (or said program storage device).

Thus the present invention discloses a process for supporting computer infrastructure, integrating, hosting, maintaining, and deploying computer-readable code into the computer system 90, wherein the code in combination with the computer system 90 is capable of performing a method for determining a pose of a subject as described herein and for performing palpation methods as described herein.

Figure 3:
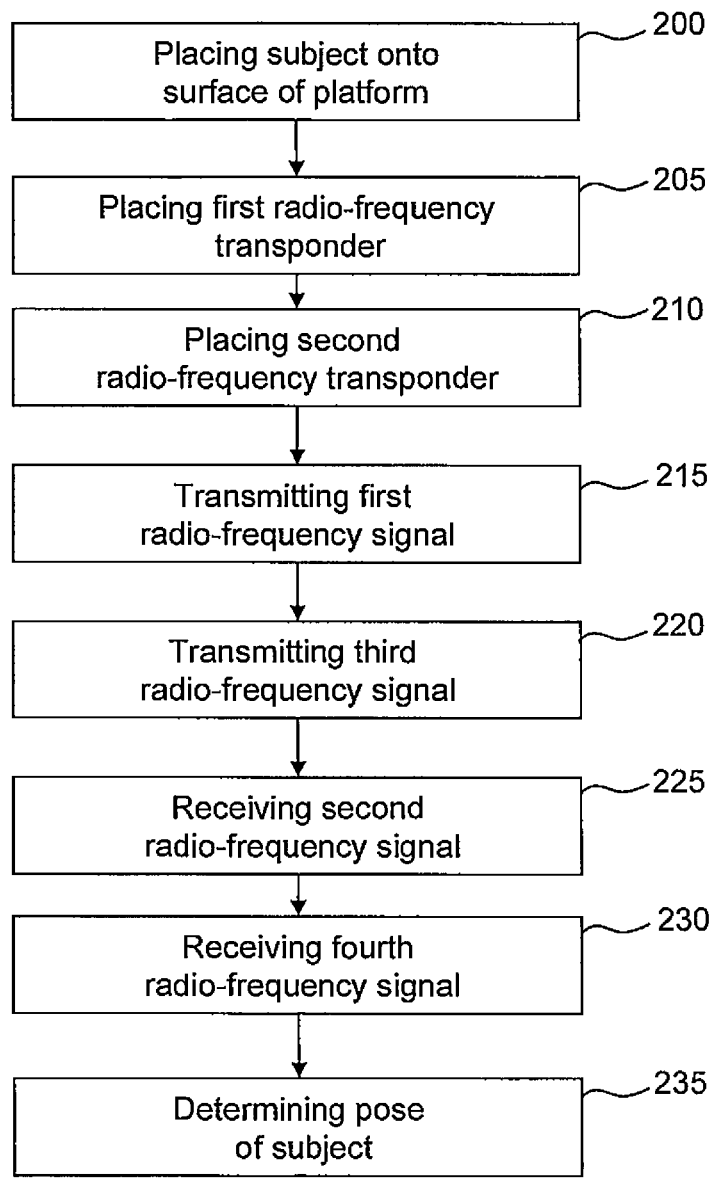
FIG. 3 is a flow chart illustrating a subject pose determining method, in accordance with embodiments of the present invention.

FIG. 3 is a flow chart illustrating a subject pose determining method. Step 200 comprises placing a subject onto a surface of a platform. The platform may comprise the support device described above and illustrated in FIG. 1. The platform may have a first end and a second end opposing the first end. The platform may be configured such that the platform may support a subject on the surface of the platform, such as a subject lying essentially horizontally for example. A first radio-frequency (RF) transceiver may be disposed at a first location on the platform, and may be operably coupled to a first antenna. A second RF transceiver may be disposed at a second location on the platform and may be operably coupled to a second antenna. The first location may comprise the first end of the platform, and the second location may comprise the second end of the platform, for example. The RF transceivers and antennas may comprise the RF transceivers and antennas described above, where the RF transceivers transmit and receive RF signals.

Step 205 comprises placing a first RF transponder onto an upper extremity of the subject. The first RF transponder may be configured such that the first RF transponder may receive a first RF signal and send a second RF signal in response to receiving said first radio frequency signal. For example, the first RF transponder may comprise an RFID tag as described above, where the tag may be placed on an upper extremity of a subject. An upper extremity as used herein is defined as a portion of a subject's body above the subject's waist, such as shoulder, arm, neck, head, wrist, chest, combinations of these, etc. The first RF transponder may comprise a microchip encoded with identifying data which identifies the first RF transponder as a transponder which is attached to an upper extremity. The first RF transponder may be placed directly onto the skin or hair of the subject, or may be placed on clothing covering the upper extremity, for example, using adhesive, straps, clips, fasteners, etc. The second RF signal transmitted by the first RF transponder may comprise a signal corresponding to the identifying data, such as data which identifies the first RF transponder as one which is located on an upper extremity of a subject, such that receiving a signal from the first transponder indicates that the first transponder and upper extremity are in close proximity to an RF transceiver receiving the signal from the first transponder.

Step 210 comprises placing a second radio-frequency transponder onto a lower extremity of the subject. The second RF transponder may be configured such that the second RF transponder may receive a third RF signal and send a fourth RF signal in response to receiving the third radio frequency signal. For example, the second RF transponder may comprise an RFID tag as described above, where the tag may be placed on a lower extremity of a subject. The term lower extremity as used herein is defined as a portion of a subject's body below the subject's waist, such as the subject's leg, knee, foot, hip, stomach, buttocks, combinations of these, etc. The second RF transponder may comprise a microchip encoded with identifying data which identifies the second RF transponder as a transponder which is attached to a lower extremity. The second RF transponder may be placed directly onto the skin or hair of the subject, or may be placed on clothing covering the lower extremity, for example, using adhesive, straps, clips, fasteners, etc. The fourth RF signal transmitted by the second RF transponder may comprise a signal corresponding to identifying data, such as data which identifies the second RF transponder as one which is located on a lower extremity of a subject, such that receiving a signal from the second transponder indicates that the second transponder and lower extremity are in close proximity to the RF transceiver receiving the signal from the second transponder.

Each of the RF transponders described herein may have a transmission range or distance, where a response RF signal sent by the RF transponder may be detected by a RF transceiver 140 near the RF transponder. As used herein, the term "near" is defined as within the transmission range of the RF transponder to which the term "near" refers. For example, a RF transponder having a transmission range of about 10 cm may transmit a RF signal, where a RF transceiver located within 10 cm of the RF transponder is described as being near the RF transponder and may detect the RF signal. Ranges of transmission may depend on signal amplitude and frequency. Signal frequencies may range from about 30 kilohertz (kHz) to about 300 kHz, such as about 125 kHz or about 134 kHz. In another example, signal frequencies may range from about 3 megahertz (MHz) to about 30 MHz, such as about 13.56 MHz. Those skilled in the art will recognize that, in general, lower frequencies result in shorter transmission ranges. Ranges of transmission for RF transponders described herein may be from about 0 cm to about 100 cm, such as from about 0 cm to about 50 cm.

Figure 4:
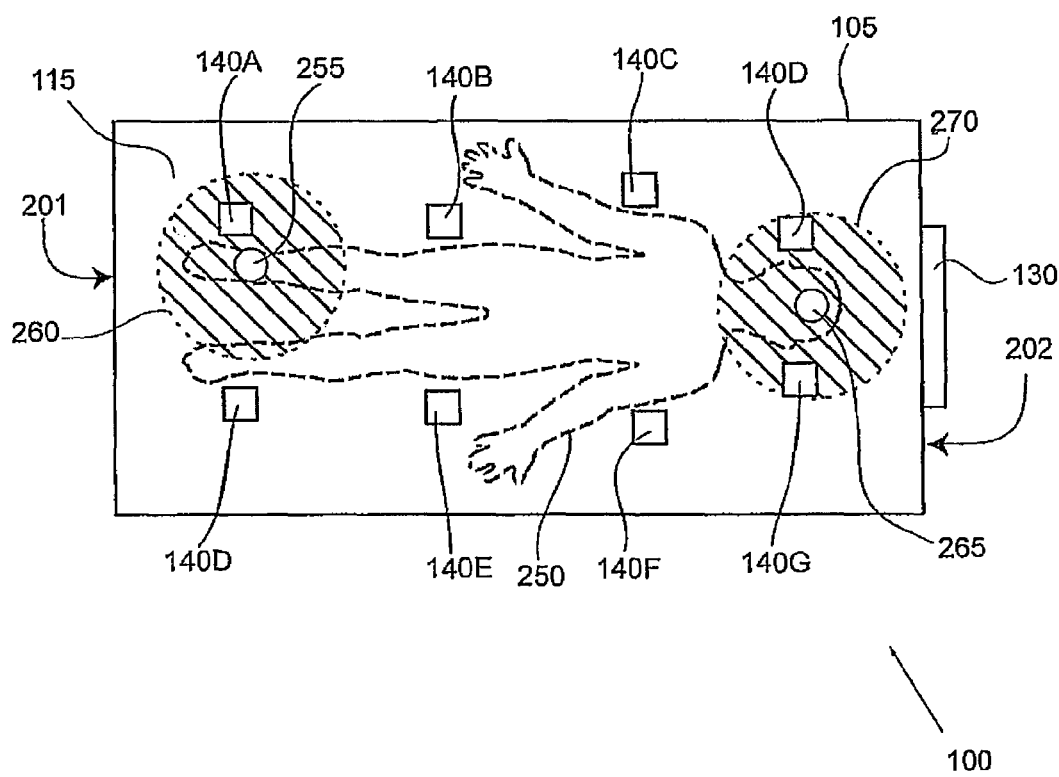
FIG. 4 is an illustration of the support device of FIG. 1 having a subject placed on the surface, in accordance with embodiments of the present invention.

FIG. 4 is an illustration of a system comprising the support device 100 of FIG. 1 having a subject 250 placed on the surface 115 of the support device 100, where the support device comprises a plurality of RF transceivers 140A, 140B, 140C, 140D, 140E, 140F, and 140G disposed on the surface 115, the support device having a first end 202 and second opposing end 201. In the example illustrated in FIG. 4, a first RF transponder 265 has been placed on an upper extremity of the subject 250, where the first RF transponder has a first transmission range 270. At least one RF transceiver, 140D and 140G, are near the first RF transponder 265 and within the first transmission range 270. RF signals transmitted from the first RF transponder 265 will be detected by the RF transceivers 140D and 140G. RF transceivers 140A, 140B, 140C, 140E, and 140F are not within the first transmission range and will not detect RF signals transmitted from the first RF transponder 265. A second RF transponder 255 has been placed on a lower extremity of the subject 250, where the second RF transponder has a second transmission range 260. At least one RF transceiver 140A is located near the second RF transponder 140A within the second transmission range 260. RF signals transmitted from the second RF transponder 255 will be detected by RF transceiver 140A. RF transceivers 140B, 140C, 140D, 140E, 140F, and 140G are not within the second transmission range and will not detect RF signals transmitted from the second RF transponder 255.

Each RF transponder described herein may comprise a computer microchip capable of being programmed and storing data, where the data may comprise information such as information about the particular RF transponder, the location of the transponder (such as on an upper extremity, lower extremity, etc.), patient information (such as name, address, government issued identification numbers, medical conditions, blood type, etc.), or a combination of these. For example, the stored data may comprise a number or series of numbers corresponding to a patient, the RF transponder, a body extremity, a combination of these, etc. The data stored within the microchip of each RF transponder may be sent to a RF transceiver as an RF signal in response to receiving a RF signal from an RF transceiver. An RF signal received by the transponder from an RF transceiver may serve as a means to provide power to the RF transponder, a means to transmit at least one command to the RF transponder, or both.

Commands sent via an RF signal by a transceiver to a RF transponder may include a command to transmit an appropriate response signal indicating which RF transceiver signal was received by the RF transponder. For example, a first RF transponder receiving a first RF signal from a first RF transceiver may be commanded by the first RF signal to transmit a second RF signal, and the first RF transponder receiving a third RF signal from a second RF transceiver may be commanded to by the third RF signal to transmit a fourth RF signal, where the second RF signal and the fourth RF signal are different. The second and fourth RF signals in this example may, for example, be used to identify which RF transceiver commanded the first RF transponder to transmit each of the second and fourth RF signals RF signal using date in each of the second and fourth RF signals. Commanding the first RF transponder may be accomplished through data transmitted in each of the first and third RF signals or by the frequency of each of the first and third signals, where the frequency of each received RF signal by the first transponder commands the first transponder to transmit an RF signal having a predetermined frequency. A computer microchip in the first transponder may be utilized to analyze each received RF signal to determine an appropriate RF signal to transmit in response, such as by using an algorithm programmed into the computer microchip.

Referring again to FIG. 3 Step 215 comprises transmitting the first RF signal from the first RF transceiver to the first RF transponder on the upper extremity of the subject, resulting in the first RF transponder sending the second RF signal to the first RF transceiver. The control system described above may direct the first RF transceiver to transmit the first signal. The RF transceivers described herein may transmit RF signals through the antenna operably coupled to the RF transceiver, and signals received by the RF transceiver may be received through the antenna. The first RF signal may have an appropriate amplitude and frequency such that the first RF transponder must be near the first RF transceiver to receive the first signal, such as in a range from about 0 cm to about 50 cm of the first RF transceiver. For example, the second RF signal may comprise data indicating that the first RF transponder is located on an upper extremity of the subject. Thus, a signal received from the first RF transponder by the first RF transceiver indicates a close proximity of the first RF transponder to the first RF transceiver (located at the first location on the platform) and that, based on the received data, the first RF transponder is located on an upper extremity of the subject, indicating that the subject's upper extremity is located in close proximity to the first location on the platform.

Step 220 comprises transmitting the third RF signal from the second RF transceiver to the second RF transponder on the lower extremity of the subject, resulting in the second RF transponder sending the fourth RF signal to the second RF transceiver. The control system described above may direct the second RF transceiver to transmit the third signal. The third RF signal may have an appropriate amplitude and frequency such that the second RF transponder must be near the second RF transceiver to receive the third RF signal, such as in a range from about 0 cm to about 50 cm of the second RF transceiver. For example, the third RF signal may comprise data indicating that the second RF transponder is located on a lower extremity of the subject. Thus, a RF signal received from the second RF transponder by the second RF transceiver indicates a close proximity of the second RF transponder (attached to a lower extremity) to the second RF transceiver (located at the second location on the platform) and that, based on the received data, the second RF transponder is located on a lower extremity of the subject, indicating that the subject's lower extremity is located in close proximity to the second location on the platform.

Step 225 comprises receiving, by the first RF transceiver, the second RF signal. Step 230 comprises receiving, by the second RF transceiver, the fourth RF signal.

Step 235 comprises determining a pose of the subject based on receiving the second RF signal and receiving the fourth RF signal. Receiving the second RF signal by the first RF transceiver indicates that the first RF transponder on the subject's upper extremity is near the first RF transceiver located at the first location on the platform. Receiving the fourth RF signal by the second RF transceiver indicates that the second RF transponder on the subject's lower extremity is near the second RF transceiver located at the second location on the platform. Thus, the subject's pose with respect to two locations on the platform may be determined, such as the subject's upper body is located at the first end of the platform and the subject's lower body is located at the second end of the platform.

The determination may allow a user remotely accessing the platform and support devices described herein to determine a subject's pose on the platform before operating other sensors and analyzing data received from different sensor unit locations on the sensor array. For example, a physician monitoring data wirelessly received from the sensor array for a patient lying on the array in a location remote from the physician, may need to know whether the signals received originate from an upper extremity or a lower extremity. The determination described above may allow such a user to make the determination without being required to directly see the patient. In another example, a nurse wirelessly monitoring a patient lying in another area of a hospital wing on an array of a support device as described here, may wish to determine if the patient is still in a correct pose for proper administration of intravenous fluids the patient is receiving. The determination described above may allow such a user to make the determination without having to leave a nurse monitoring station. Similarly, a medical technician flying a medical evacuation helicopter may need to determine a patient has remained in a secure pose while being transported in the helicopter. Such a user may be able to make the determination without looking away from the controls of the aircraft or leaving the pilot's seat using the method described herein.

The platform further may further comprise a computer system, such as the computer system described above for example, operably coupled to the first radio-frequency transceiver and the second radio-frequency transceiver. The computer system may be part of the control system described above. The computer system may be physically connected to the transceivers, or may be wirelessly coupled to the transceivers such as through a wireless telecommunication connection, for example. Determining a pose of the subject may include receiving data from the first and second radio-frequency transceivers by the computer system, where the data corresponds to the second and fourth radio-frequency signals. The computer may then analyze the received data and determine, based on the analyzing that the first radio-frequency transponder on the upper extremity of the subject is located near the first radio-frequency transceiver disposed on the first end, and that the second radio-frequency transponder on the lower extremity of the subject is located near the second radio-frequency transceiver disposed on the second end. Analyzing may comprise comparing the received data to known values stored in memory representing identifying information for each transponder, such as a serial number, signal frequency, location on the platform, etc.

Figure 5:
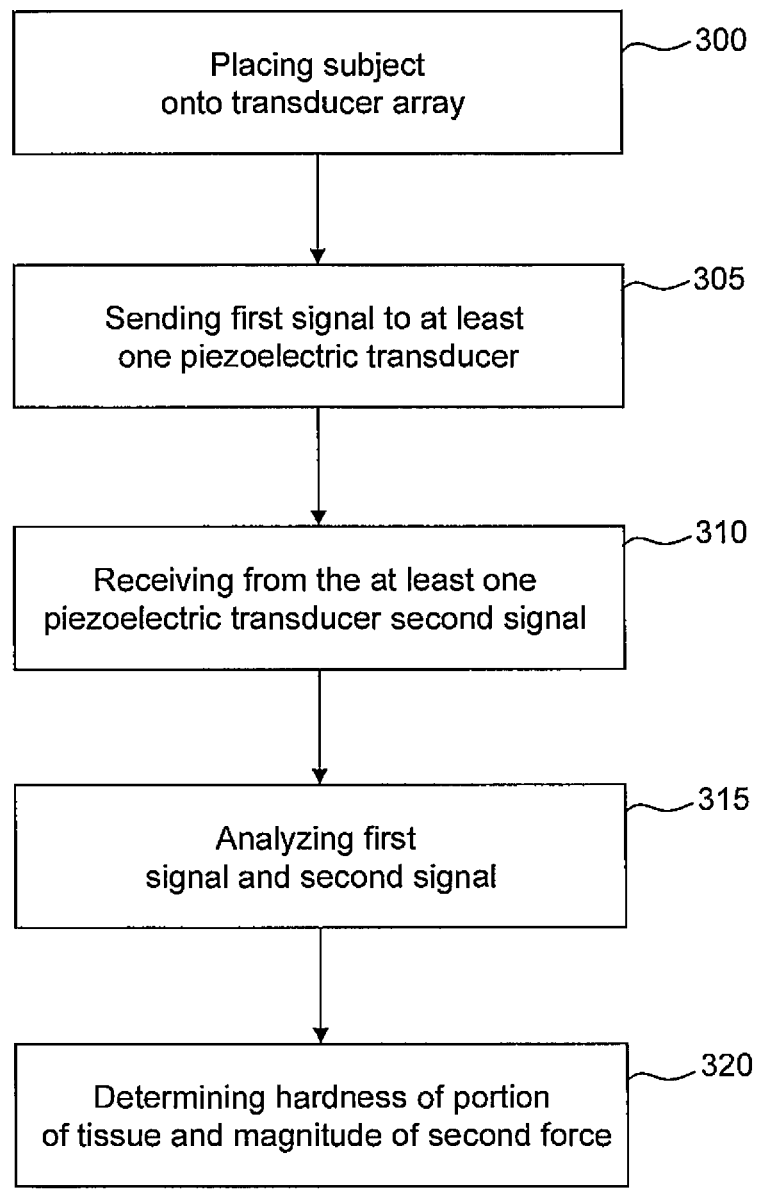
FIG. 5 is a flow chart illustrating a palpation method, in accordance with embodiments of the present invention.

FIG. 5 is a flow chart illustrating a palpation method. The method may permit a user to palpate a subject without making direct physical contact with the subject, such as from a remote location. For example, a victim of biological or chemical contamination may be located in an isolation area or otherwise remotely located, where direct contact with the victim/patient poses a hazard to the examining medical personnel. The examining individual may wish to palpate areas of the patient's external tissue to determine the extent of injuries, such as swelling, inflammation, tissue trauma, etc. The user may remotely palpate a subject after determining a pose of the subject as described in the steps above.

Step 300 comprises placing a subject onto a transducer array disposed on a surface of a support device. The support device may be a support device such as described above and may support a subject, such as in an essentially horizontal pose. As described herein, the support device may function as a palpation device for performing a palpation method (vide infra). The support device may comprise at least two RF transceivers as described above. The transducer array may be disposed between the support device and the subject, where the transducer array may comprise a plurality of piezoelectric transducers, such as the sensor array described above comprising a plurality of sensor units each comprising a piezoelectric transducer. For example, a patient may be made to lay down on the sensor array of a gurney comprising the support device described above, where the patient's full weight rests on the transducer array.

Step 305 comprises sending a first signal to at least one piezoelectric transducer of the plurality of piezoelectric transducers, where the at least one piezoelectric transducer is in direct contact with a portion of external tissue of the subject, resulting in the at least one piezoelectric transducer actuating and exerting a first force against the portion of external tissue. For example, the first signal may be sent by a user using a control system such as is described above, where the first signal may direct the at least one piezoelectric transducer to actuate and press against the tissue of the subject resting against the at least one piezoelectric transducer. The at least one piezoelectric transducer may comprise two or more transducers, such as 10, 20, 30, or all transducers in the array, for example. The numbers of piezoelectric transducers used may be determined by the size of the area a user wishes to palpate.

Step 310 comprises receiving from the at least one piezoelectric transducer a second signal in response to exerting the first force against the portion of external tissue, where the second signal results from a second force exerted against the at least one piezoelectric transducer in response to the at least one piezoelectric transducer exerting the first force. For example, when the at least one piezoelectric transducer exerts the first force against the tissue of a subject, the tissue may have a particular density and pliability or hardness. The resistance of the subject's tissue to indentation by the at least one transducer is a resistive force directed back against the transducer, generating the second signal transmitted from the piezoelectric transducer. The second signal may be received by a user, such as through a control system coupled to the transducer array, where the control system may be configured as described above.

The method of FIG. 5 may further comprise steps 315 and step 320. Step 315 comprises analyzing the second signal and the first signal. Analyzing may comprise analyzing using a computer algorithm in a computer system, such as the computer system described above, capable of converting the signals into data representing the signals, where the computer system may be coupled to the support device. For example, the support device may comprise a control system, as described above, coupled to the transducer array where the control system may direct each piezoelectric transducer of the at least one piezoelectric transducer to actuate. The support device may comprise a communication device operably coupled to the control system, where the communication device may receive commands from a remote source and relay commands to the control system. The computer system may be a remote computer system where the computer system may be coupled via a wireless or wired connection to the support device such as through the communication device.

For example before sending the first signal in step 305, a first command may be received by the communication device, such as from a user, external computer system, or a control system transmitting commands to the communication device for directing the operation of the transducer array. Commands received by the communication device may comprise wired communications, wireless communications, or combination of these. The communication device may relay the first remote command to the control system, resulting in the control system directing the at least one piezoelectric transducer to actuate, where directing comprises sending the first signal to the at least one piezoelectric transducer.

Step 320 of FIG. 5 comprises determining, based on said analyzing, a hardness of the portion of external tissue and a magnitude of the second force exerted by the portion of external tissue. Determining may comprise calculating, by a computer algorithm or by a user, the hardness of the portion of external tissue based on data relating to signals from the piezoelectric transducer, such as the amount of force required to indent the portion of tissue by moving the piezoelectric transducer a specified distance, the amount of resistive force exerted by the portion of external tissue upon indentation by the piezoelectric transducer, or a combination of these. Tissue which has a large degree of swelling or inflammation may show a higher degree of resistive force (higher hardness) than normal healthy tissue. Tissue which has a large degree of trauma or damage or blood loss, may exhibit a lower resistive force (lower hardness) than normal tissue. The hardness determine in step 320 and data relating to signals received from the piezoelectric transducers may be stored in the computer memory, may be output through an output device such as described above, or a combination of these.

The foregoing description of the embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

What is claimed:

1. A method for determining a pose of a subject, said method comprising:

placing transponders on the subject disposed on a surface of a platform, wherein a totality of the transponders consist of a first radio-frequency transponder and a second radio-frequency transponder placed onto an upper extremity and a lower extremity, respectively, of the subject, and wherein a first radio-frequency transceiver is located at a first location on the surface and a second radio-frequency transceiver is located at a second location on the surface;

transmitting a first radio-frequency signal from the first radio-frequency transceiver to the first radio-frequency transponder on the upper extremity of the subject, resulting in the first radio-frequency transponder sending a second radio-frequency signal to the first radio-frequency transceiver;

receiving, by the first radio-frequency transceiver, the second radio-frequency signal;

receiving, by the second radio-frequency transceiver, a fourth radio-frequency signal transmitted by the second radio-frequency transponder in response to the second radio-frequency transponder having previously received a third radio-frequency signal from the second radio-frequency transceiver; and determining the pose of the subject based on said receiving the second radio-frequency signal and said receiving the fourth radio-frequency signal.

2. The method of claim 1, wherein the method further comprises storing data in the first radio-frequency transponder, and wherein the second radio-frequency signal sent by the first radio-frequency transponder to the first radio-frequency transceiver comprises the stored data.

3. The method of claim 2, wherein the stored data comprises information about the first radio-frequency transponder and a location of the first radio-frequency transponder.

4. The method of claim 2, wherein the stored data comprises patient information pertaining to the subject.

5. The method of claim 4, wherein the patient information comprises a name of the subject, an address of the subject, a government issued identification number of the subject, and a medical condition of the subject.

6. The method of claim 5, wherein the patient information further comprises a blood type of the subject.

7. The method of claim 2, wherein the subject is a patient, and wherein the stored data comprises a series of numbers corresponding to the patient, the first radio-frequency transponder, and a body extremity of the patient.

8. The method of claim 7, wherein the stored data comprises a series of numbers corresponding to the patient, the first radio-frequency transponder, and a body extremity of the patient.

9. The method of claim 1, wherein the subject is a human being.

10. The method of claim 9, wherein the upper extremity and lower extremity respectively comprise a head and a leg of the subject, and wherein the first radio-frequency transponder and the second radio-frequency transponder are respectively placed onto the head and the leg of the subject.

11. A system for determining a pose of a subject, said system comprising:
a platform having a surface, wherein the subject is disposed on the surface;
transponders placed on the subject, wherein a totality of the transponders consist of a first radio-frequency transponder and a second radio-frequency transponder placed onto an upper extremity and a lower extremity, respectively, of the subject;
a first radio-frequency transceiver located at a first location on the surface;
a second radio-frequency transceiver located at a second location on the surface;
means for transmitting a first radio-frequency signal from the first radio-frequency transceiver to the first radio-frequency transponder on the upper extremity of the subject, resulting in the first radio-frequency transponder sending a second radio-frequency signal to the first radio-frequency transceiver;
means for receiving, by the first radio-frequency transceiver, the second radio-frequency signal;
means for receiving, by the second radio-frequency transceiver, a fourth radio-frequency signal transmitted by the second radio-frequency transponder in response to the second radio-frequency transponder having previously received a third radio-frequency signal from the second radio-frequency transceiver; and
means for determining the pose of the subject based on receiving the second radio-frequency signal and receiving the fourth radio-frequency signal.

12. The system of claim 11, wherein the first radio-frequency transponder comprises data stored therein, and wherein the second radio-frequency signal comprises the stored data.

13. The system of claim 12, wherein the first radio-frequency transponder comprises a computer microchip in which an algorithm is programmed, and wherein execution of the algorithm performs a process, said process comprising:
inserting the stored data into the second radio-frequency signal.

14. The system of claim 13, said process further comprising:
performing an analysis of the first radio-frequency signal received by the first radio-frequency transponder from the first radio-frequency transceiver to determine that the second radio-frequency signal is to comprise the stored data.

15. The system of claim 14, wherein said inserting the stored data into the second radio-frequency signal is performed in response to the performed analysis.

16. The system of claim 12, wherein the stored data comprises information about the first radio-frequency transponder and a location of the first radio-frequency transponder.

17. The system of claim 12, wherein the stored data comprises patient information pertaining to the subject, wherein the patient information comprises a name of the subject, an address of the subject, a government issued identification number of the subject, and a medical condition of the subject.

18. The system of claim 17, wherein the patient information further comprises a blood type of the subject.

19. The system of claim 12, wherein the subject is a patient, and wherein the stored data comprises a series of numbers corresponding to the patient, the first radio-frequency transponder, and a body extremity of the patient.

20. The system of claim 11, wherein the subject is a human being.

* * * * *